US007105713B2

(12) United States Patent
Ghosh et al.

(10) Patent No.: US 7,105,713 B2
(45) Date of Patent: Sep. 12, 2006

(54) PREPARATION OF ALKYL-AROMATIC PRODUCTS

(75) Inventors: Ashim Kumar Ghosh, Houston, TX (US); Pamela Harvey, Missouri City, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 11/147,732

(22) Filed: Jun. 8, 2005

(65) Prior Publication Data

US 2005/0277795 A1 Dec. 15, 2005

Related U.S. Application Data

(62) Division of application No. 10/864,021, filed on Jun. 9, 2004, now abandoned.

(51) Int. Cl.
*C07C 2/68* (2006.01)
(52) U.S. Cl. ...................................... 585/462; 585/446
(58) Field of Classification Search ............... 585/446, 585/462
See application file for complete search history.

(56) References Cited

U.S. PATENT DOCUMENTS

| | | | |
|---|---|---|---|
| 3,965,207 A | 6/1976 | Weinstein | |
| 4,520,219 A * | 5/1985 | Sato | 585/462 |
| 4,548,914 A | 10/1985 | Chu | |
| 4,590,321 A | 5/1986 | Chu | |
| 4,623,530 A | 11/1986 | Cullo et al. | |
| 4,623,533 A | 11/1986 | Broecker et al. | |
| 4,638,106 A | 1/1987 | Pieters et al. | |
| 4,665,251 A | 5/1987 | Chu | |
| 4,670,616 A | 6/1987 | De Simone et al. | |
| 4,673,767 A | 6/1987 | Nimry et al. | |
| 4,694,114 A | 9/1987 | Chu et al. | |
| 4,695,666 A | 9/1987 | Chao et al. | |
| 4,695,667 A | 9/1987 | Sumitani et al. | |
| 4,704,495 A | 11/1987 | Dessau | |
| 4,716,135 A | 12/1987 | Chen | |
| 4,721,827 A | 1/1988 | Cullo et al. | |
| 4,727,209 A | 2/1988 | Chao | |
| 4,746,763 A | 5/1988 | Kocal | |
| 4,758,328 A | 7/1988 | Young | |
| 4,761,513 A | 8/1988 | Steacy | |
| 4,847,223 A | 7/1989 | Le Van Mao et al. | |
| 4,861,930 A | 8/1989 | Cottrell et al. | |
| 4,873,067 A | 10/1989 | Valyocsik et al. | |
| 4,891,197 A | 1/1990 | Derouane et al. | |
| 4,891,467 A | 1/1990 | Sikkenga | |
| 4,902,406 A | 2/1990 | Valyocsik | |
| 4,912,073 A | 3/1990 | Chu | |
| 4,914,067 A | 4/1990 | Pellet et al. | |
| 4,935,574 A | 6/1990 | D'Amore et al. | |
| 4,943,545 A | 7/1990 | Chang et al. | |
| 4,962,255 A | 10/1990 | Fraenkel et al. | |
| 4,973,781 A | 11/1990 | Valyocsik et al. | |
| 5,041,402 A | 8/1991 | Casci et al. | |
| 5,043,502 A | 8/1991 | Martindale et al. | |
| 5,047,141 A | 9/1991 | Chu | |
| 5,068,483 A | 11/1991 | Barthomeuf et al. | |
| 5,094,995 A | 3/1992 | Butt et al. | |
| 5,105,047 A | 4/1992 | Waller | |
| 5,108,579 A | 4/1992 | Casci | |
| 5,110,776 A | 5/1992 | Chitnis et al. | |
| 5,124,299 A | 6/1992 | Waller | |
| 5,171,921 A | 12/1992 | Gaffney et al. | |
| 5,173,461 A | 12/1992 | Absil et al. | |
| 5,178,748 A | 1/1993 | Casci et al. | |
| 5,231,064 A | 7/1993 | Absil et al. | |
| 5,233,102 A | 8/1993 | Butt et al. | |
| 5,246,688 A | 9/1993 | Faust et al. | |
| 5,248,841 A | 9/1993 | Young | |
| 5,254,767 A | 10/1993 | Dwyer | |
| 5,254,770 A | 10/1993 | Olson et al. | |
| 5,294,578 A | 3/1994 | Ho et al. | |
| 5,315,033 A | 5/1994 | Butt et al. | |
| 5,318,696 A | 6/1994 | Kowalski | |
| 5,321,183 A | 6/1994 | Chang et al. | |
| 5,336,478 A | 8/1994 | Dwyer et al. | |
| 5,345,021 A | 9/1994 | Casci et al. | |
| 5,348,643 A | 9/1994 | Absil et al. | |
| 5,349,113 A | 9/1994 | Chang et al. | |
| 5,365,003 A | 11/1994 | Chang et al. | |
| 5,366,948 A | 11/1994 | Absil et al. | |
| 5,367,100 A | 11/1994 | Gongwei et al. | |

(Continued)

OTHER PUBLICATIONS

Kaeding, W.W., et al., Selective Alkylation of Toluene to Produce para-Xylene, Journal of Catalysis, 1981, pp. 159-174, vol. 67.

(Continued)

*Primary Examiner*—Elizabeth D. Wood
(74) *Attorney, Agent, or Firm*—Grady K. Bergen; Jim D. Wheelington

(57) ABSTRACT

A method of modifying a ZSM-5-type zeolite catalyst to increase selectivity of the catalyst for para-isomers in aromatic alkylation reactions is provided. The method includes contacting a ZSM-5-type zeolite catalyst with a fluoride-containing compound. The fluoride-containing zeolite catalyst can be used in aromatic alkylation to provide di-alkyl aromatic products. A method of preparing a xylene product is also accomplished by providing a fluoride-treated ZSM-5-type zeolite catalyst within a reactor. The fluoride-treated ZSM-5 zeolite catalyst is contacted with a toluene/methanol feed under reaction conditions conditions suitable for toluene methylation to form a xylene product containing at least 50% para-xylene by total mixed xylenes.

19 Claims, No Drawings

U.S. PATENT DOCUMENTS

| | | |
|---|---|---|
| 5,371,307 A | 12/1994 | Guth et al. |
| 5,378,670 A | 1/1995 | Kumar |
| 5,380,690 A | 1/1995 | Zhicheng et al. |
| 5,385,718 A | 1/1995 | Casci et al. |
| 5,399,336 A | 3/1995 | Guth et al. |
| 5,430,212 A | 7/1995 | Butt et al. |
| 5,430,213 A | 7/1995 | Hendriksen et al. |
| 5,446,234 A | 8/1995 | Casci et al. |
| 5,455,213 A | 10/1995 | Chang et al. |
| 5,456,821 A | 10/1995 | Absil et al. |
| 5,464,799 A | 11/1995 | Casci et al. |
| 5,475,179 A | 12/1995 | Chang et al. |
| 5,498,814 A | 3/1996 | Chang et al. |
| 5,503,818 A | 4/1996 | Nicolaides |
| 5,516,736 A | 5/1996 | Chang et al. |
| 5,523,510 A | 6/1996 | Pellet et al. |
| 5,534,239 A | 7/1996 | Fajula et al. |
| 5,536,894 A | 7/1996 | Degnan et al. |
| 5,541,146 A | 7/1996 | Chang et al. |
| 5,561,095 A | 10/1996 | Chen et al. |
| 5,563,310 A | 10/1996 | Chang et al. |
| 5,569,805 A | 10/1996 | Beck et al. |
| 5,571,768 A | 11/1996 | Chang et al. |
| 5,573,746 A | 11/1996 | Chen |
| 5,576,256 A | 11/1996 | Monque et al. |
| 5,607,888 A | 3/1997 | Chang et al. |
| 5,607,890 A | 3/1997 | Chen et al. |
| 5,646,314 A | 7/1997 | Crocco et al. |
| 5,648,580 A | 7/1997 | Chen et al. |
| 5,658,454 A | 8/1997 | Absil et al. |
| 5,675,047 A | 10/1997 | Beck et al. |
| 5,689,024 A | 11/1997 | Schmitt |
| 5,698,756 A | 12/1997 | Beck et al. |
| 5,780,563 A | 7/1998 | Chen et al. |
| 5,789,335 A | 8/1998 | Chen et al. |
| 5,811,613 A | 9/1998 | Bhat et al. |
| 5,833,840 A | 11/1998 | Absil et al. |
| 5,902,919 A | 5/1999 | Chen et al. |
| 5,905,051 A | 5/1999 | Wu et al. |
| 5,922,922 A | 7/1999 | Harris et al. |
| 5,925,586 A | 7/1999 | Sun |
| 5,939,597 A | 8/1999 | Dessau et al. |
| 5,951,963 A | 9/1999 | He et al. |
| 5,955,641 A | 9/1999 | Chen et al. |
| 5,994,603 A | 11/1999 | Mohr et al. |
| 6,034,283 A | 3/2000 | Ban et al. |
| 6,040,257 A | 3/2000 | Drake et al. |
| 6,046,128 A | 4/2000 | Kisen et al. |
| 6,047,544 A | 4/2000 | Yamamoto et al. |
| 6,048,816 A | 4/2000 | Brown et al. |
| 6,060,633 A | 5/2000 | Chen et al. |
| 6,074,975 A | 6/2000 | Yao et al. |
| 6,080,303 A | 6/2000 | Cao et al. |
| 6,080,698 A | 6/2000 | Zhang et al. |
| 6,083,865 A | 7/2000 | Drake et al. |
| 6,090,274 A | 7/2000 | Wu et al. |
| 6,100,437 A | 8/2000 | Koehl et al. |
| 6,124,227 A | 9/2000 | Yao et al. |
| 6,150,293 A | 11/2000 | Verduijn et al. |
| 6,156,949 A | 12/2000 | Brown et al. |
| 6,160,191 A | 12/2000 | Smith et al. |
| 6,187,982 B1 | 2/2001 | Beck et al. |
| 6,211,104 B1 | 4/2001 | Shi et al. |
| 6,217,748 B1 | 4/2001 | Hatanaka et al. |
| 6,251,263 B1 | 6/2001 | Hatanaka et al. |
| 6,294,493 B1 | 9/2001 | Strohmaier et al. |
| 6,300,535 B1 | 10/2001 | van den Berge et al. |
| 6,306,790 B1 | 10/2001 | Rodriguez et al. |
| 6,316,379 B1 | 11/2001 | Mao |
| 6,331,500 B1 | 12/2001 | Tsuji et al. |
| 6,342,153 B1 | 1/2002 | Guan et al. |
| 6,388,156 B1 | 5/2002 | Ou et al. |
| 6,395,664 B1 | 5/2002 | Boehner et al. |
| 6,399,530 B1 | 6/2002 | Chen et al. |
| 6,417,421 B1 | 7/2002 | Yao |
| 6,423,879 B1 | 7/2002 | Brown et al. |
| 6,444,610 B1 | 9/2002 | Yamamoto |
| 6,459,006 B1 | 10/2002 | Ou et al. |
| 6,469,095 B1 | 10/2002 | Gareiss et al. |
| 6,503,862 B1 | 1/2003 | Yamamoto |
| 6,504,072 B1 | 1/2003 | Brown et al. |
| 6,504,074 B1 | 1/2003 | Verduijn et al. |
| 6,506,954 B1 | 1/2003 | Brown et al. |
| 6,518,213 B1 | 2/2003 | Yamamoto et al. |
| 6,548,725 B1 | 4/2003 | Froment et al. |
| 6,566,293 B1 | 5/2003 | Vogt et al. |
| 6,589,901 B1 | 7/2003 | Yamamoto |
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B1 | 2/2004 | Williams et al. |
| 6,699,811 B1 | 3/2004 | Mohr et al. |
| 6,723,297 B1 | 4/2004 | Chen et al. |
| 6,726,834 B1 | 4/2004 | Quesada et al. |
| 6,770,251 B1 | 8/2004 | Yoshikawa |
| 6,773,694 B1 | 8/2004 | Lesch et al. |
| 6,799,089 B1 | 9/2004 | Toulhoat |
| 6,811,684 B1 | 11/2004 | Mohr et al. |
| 6,812,181 B1 | 11/2004 | van der Berge et al. |

OTHER PUBLICATIONS

Niwa, M., et al., Fine Control of the Pore-Opening Size of Zeolite ZSM-5 by Chemical Vapor Deposition of Silicon Methoxide, J. Phys. Chem., 1986, pp. 6233-6237, vol. 90.

Ghosh, A.K., et al., Fluorine-Promoted Catalysts, Catal. Rev.-Sci. Eng., 1985, pp. 539-589, vol. 27(4).

Ghosh, A.K., et al., An Infrared Study of the Effect of HF Treatment on the Acidity of ZSM-5, Zeolites, 1990, pp. 766-771, vol. 10.

* cited by examiner

PREPARATION OF ALKYL-AROMATIC PRODUCTS

This application is a division of U.S. patent application Ser. No. 10/864,021, entitled "Fluoride-Modified Zeolite Catalyst and Method," filed Jun. 9, 2004, which is herein incorporated by reference in its entirety.

TECHNICAL FIELD

The invention relates generally to the alkylation of aromatic compounds and catalysts used for such reactions.

BACKGROUND

Para-xylene is a valuable substituted aromatic compound because of its great demand for its oxidation to terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalyst, particularly over zeolite or zeolite-type catalyst. In particular, ZSM-5-type zeolite, zeolite Beta and silicaaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

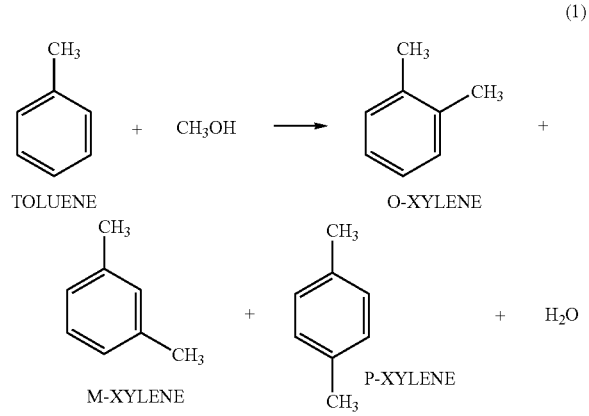

Thermodynamic equilibrium compositions of o-, m-, and p-xylenes may be around 25, 50 and 25 mole %, respectively, at a reaction temperature of about 500° C. Such toluene methylation may occur over a wide range of temperatures, however. Para-xylene can be separated from mixed xylenes by a cycle of adsorption and isomerization. Byproducts such as C9+ and other aromatic products can be produced by secondary alkylation of the xylene product.

A significantly higher amount of p-xylene can be obtained in toluene methylation reaction if the catalyst has shape selective properties. Shape selective properties can be obtained in modified zeolite catalysts by narrowing zeolite pore opening size, inactivation of the external surface of the zeolite or controlling zeolite acidity. Toluene methylation may occur over a modified ZSM-5 or ZSM-5-type zeolite catalyst giving xylene products containing significantly greater amounts of p-xylene than the thermodynamic concentration.

Phosphoric acid and other phosphorus-containing compounds have been used to modify ZSM-5 zeolite catalysts to provide shape selective properties. U.S. Pat. No. 6,504,072, for instance, discloses the treatment of ZSM-5 zeolite catalyst with phosphorus to control the reduction of diffusivity and pore volume prior to severe steaming to provide a para-selective catalyst. U.S. Pat. No. 4,554,394 discusses the treatment of ZSM-5 zeolites with a vapor phase organophosphorus reagent to provide para-selective properties. In Kaeding, et al, *Selective Alkylation of Toluene with Methanol to Produce para-Xylene*, Journal of Catalysis, Vol. 67, pp. 159–174 (1981), a procedure of making a ZSM-5 catalyst by incorporating 5% phosphorus was described in which the catalyst was impregnated with a solution of diphenylphosphinous acid in toluene. The ZSM-5 catalyst thus modified showed toluene methylation activity with 84–90% para isomer in the xylene product. In another procedure, a catalyst was modified by incorporating 8.51% phosphorus from an aqueous phosphoric acid reagent. The catalyst showed p-xylene selectivity as high as 97%, however, the catalyst showed a decreasing activity within hours due to coke deposition.

Unfortunately, there are a number of technical hurdles for toluene methylation to be commercially successful and improvements are needed.

DETAILED DESCRIPTION

It has been found that increased selectivity for para-isomers of dialkylated aromatic products can be obtained over ZSM-5-type zeolite catalysts after treating with a fluoride-containing compound. As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in any limiting sense.

EXAMPLES 1–67

The catalysts A–E, as referenced in Table 1 and prepared as described above, were used in toluene methylation reactions. The reactions were each carried out in a fixed bed, continuous flow type reactor. In each case, the catalyst used was dried by slowly raising to catalyst bed temperature (about 5° C./min) to 200° C. under hydrogen ($H_2$) flow for at least one hour. A premixed toluene and methanol feed (molar ratio 2/1) was added to the reactor at 200° C. and the catalyst bed inlet temperature was increased to about 500° C. The liquid hourly space velocity (LHSV) based on toluene/methanol feed was maintained at about 31 $hr^{-1}$ and cofeed of $H_2$ gas was fed and maintained to provide a $H_2$/(toluene+methanol) molar ratio of about 0.1. Water was added to the hydrocarbon (HC, where HC=taluene+methanol) feed and was vaporized prior to introduction into the reactor. The $H_2O$/HC molar ratio was about 0.65 and the reactor pressure was about 20 psig. The following results were obtained, as presented in Table 2 below.

Although specific reference is made to the use of the modified catalyst in toluene methylation, for which the modified zeolite is particularly well suited, it will be apparent to those skilled in the art that the catalyst may have application for use in other types of reactions, such as transalkylation and other aromatic alkylation reactions. In particular, the catalyst of the invention may have application to such reactions to provide increased selectivity for para-isomer in mixed dialkylated aromatic products.

As used herein, catalytic activity for toluene methylation can be expressed as the % moles of toluene converted with respect to the moles of toluene fed and can be defined as:

$$\text{Mole \% Toluene Conversion} = [(T_i - T_o)/T_i] \times 100 \quad (2)$$

where, $T_i$ is the number of moles of toluene fed and $T_o$ is the number of moles toluene unreacted. As used herein, selectivity for total xylenes may be expressed as:

$$\text{Mole \% Total Xylene Selectivity} = [X_{tx}/(T_i - T_o)] \times 100 \quad (3)$$

where, $X_{tx}$ is the number of moles of total (o-, m- or p-) xylenes in the product.

As used herein, selectivity for p-xylene may be expressed as:

$$\text{Mole \% p-Xylene Selectivity} = (X_p/X_{tx}) \times 100 \quad (4)$$

where, $X_p$ is the number of moles of p-xylene.

The fluorided-zeolite catalyst may be made by incorporating fluoride in zeolite by vapor phase fluoridation or liquid impregnation. See A. K. Ghosh and R. A. Kydd, *Fluorine-Promoted Catalysts*, Catal. Rev.-Sci. Eng., 1985, pp. 539–589 Vol. 27(4), which is herein incorporated by reference. In vapor phase fluoridation, the zeolite is maintained in contact with vapors of a fluoride-containing compound at a temperature between 100° C. and 500° C. Impregnation is carried out by saturating the zeolite with a solution containing an appropriate amount of fluoride-containing compound and then evaporating the liquid. The fluoride-containing compound may include $F_2$, HF, $BF_3$, $NH_4F$, $NH_4BF_4$, $CF_4$, $CHF_3$, $CH_2F_2$, $CF_3COOH$, $CF_3OH$, $CF_3OCF_3$, $CF_3CH_2OH$, $SF_6$, $SO_2F_2$, $SOF_2$ or $NH_4SiF_6$. One or more different fluoride-containing compounds may be used to treat the zeolite catalyst, either simultaneously, as a single mixture or sequentially. The amount of fluoride used may provide a fluoride content of the treated catalyst of from 0.05 wt % F or more as measured by using ASTM E-442 (Oxygen Flask Combustion and Ion-Selective Electrode) method.

The starting zeolite may be an $NH_4$- or H-form ZSM-5 zeolite, which may be in the form of a powder or any other form. The zeolite catalyst may be prepared by treating a slurry of the zeolite with an aqueous solution of the fluoride-containing compound. All liquid in the zeolite slurry with the fluoride containing compound may be evaporated at a temperature between room temperature to about 70° C., although higher temperatures may be used. The slurry may also be stirred or agitated during this step to ensure uniform treatment. The slurry may be heated until all liquids are evaporated.

The fluoride-modified zeolite catalyst may be used unbound or be bound with a binder. Examples of suitable binders include such materials as alumina, clay, and silica. Those techniques used for preparing the bound catalyst are well known in the art. The catalyst, bound or unbound, may be calcined at a temperature between 400° C. and 570° C. in an environment containing oxygen, typically air.

The resulting fluoride-treated ZSM-5 zeolite catalyst may show a slight decrease in both BET surface area (SA) and total pore volume (PV), as measured by $N_2$ adsorption, compared to the same untreated ZSM-5 zeolite catalyst. The fluoride treated catalyst may have a BET surface area of 350 $m^2/g$ or less, more particularly 330 $m^2/g$ or less, and still more particularly 300 $m^2/g$ or less, and may have a pore volume of about 0.25 ml/g or less.

The modified catalyst may be contacted with an appropriate feed under alkylation reaction conditions to carry out aromatic alkylation. Examples of alkylation reactions for which the invention has application include toluene alkylation with an alkylating agent such as methanol. Other alkylation reactions may include transalkylation, such as gas phase toluene disproportionation in the presence of hydrogen to produce benzene and mixed xylenes.

The reactor pressure for toluene methylation or other aromatic alkylation may vary, but typically ranges from about 10 to about 1000 psig.

The reaction may be carried in a variety of different reactors that are commonly used for carrying out aromatic alkylation reactions. Single or multiple reactors in series and/or parallel are suitable for carrying out the toluene methylation or other aromatic alkylation reactions.

In particular, the modified catalyst is useful in toluene methylation for preparing a xylene product from a feed of toluene and methanol that has increased selectivity for p-xylene. In such reactions, water may be introduced with the feed in an amount of at least 0.1 moles water per mole of toluene/methanol feed, as described in U.S. patent application Ser. No. 10/675,780, filed Sep. 30, 2003, which is herein incorporated by reference. A hydrogen cofeed is also used. The hydrogen may be used in an amount of at least 1.0 mole per mole of toluene/methanol feed.

The fluoride-treated zeolite catalyst may exhibit at least a 50% increase in selectivity for para-isomers in aromatic alkylation reactions compared to the same zeolite catalyst without such treatment under similar aromatic alkylation reaction conditions. When ZSM-5-type zeolite catalysts modified in accordance with the invention are used in toluene methylation, a mixed xylene product having a p-xylene content of 50%, 60%, 70% or more by total moles of xylene may be obtained.

The following examples further illustrate the invention.

EXAMPLES

Catalyst Preparation

Catalyst A–D

To form each catalyst, a slurry of HZSM-5 zeolite powder having a $SiO_2/Al_2O_3$ mole ratio of about 280 in deionized water was prepared in a beaker. The beaker was placed on a hot plate and the zeolite suspension was stirred using a magnetic stir bar. Hydrofluoric acid (40% in water) was slowly added to the slurry. In certain cases, the HF solution was further diluted by adding water prior to adding to the zeolite slurry. The temperature of the zeolite suspension (or slurry) was maintained at <70° C. All liquid was evaporated at a temperature below 70° C. The zeolite was then dried at about 90° C. at least for 4 hours and then was calcined in air at approximately 510° C. for 10 hrs. The HF treated and calcined zeolite was then pressed to form pellets and was crushed and sized using 20 and 40 mesh screens.

A series of catalysts A–D were prepared using the above technique by varying the amount of hydrofluoric acid with respect to the amount of starting HZSM-5 powder. The amount of zeolite, water (to form slurry), aqueous HF and additional water (to dilute HF further, if any) are shown in Table 1. The BET surface area and total pore volume (measured by $N_2$ adsorption) for catalysts A–D are presented in Table 1 below.

Comparative Catalyst E

A non-modified HZSM-5 zeolite catalyst (Catalyst E) was also tested. The starting material was an $NH_4$-ZSM-5 zeolite powder having a $SiO_2/Al_2O_3$ mole ratio of 280. The zeolite powder was calcined at 530° C. under air for 10 hr and then pressed and sized using 20 and 40 mesh screens for use in a reactor for toluene methylation reaction. BET surface area and total pore volume (measured by $N_2$ adsorption) for catalyst E are presented in Table 1 below.

Comparative Catalyst F

A $H_2SO_4$ treated $NH_4$-ZSM-5 zeolite catalyst (Catalyst F) was also tested. The starting material was an $NH_4$-ZSM-5 zeolite powder having a $SiO_2/Al_2O_3$ mole ratio of 280. A zeolite slurry was made by adding 25.33 g of the zeolite and 50 ml water. The slurry was heated and continuously stirred. 10.41 g of $H_2SO_4$ (95–98%) was added to the zeolite slurry when its temperature was about 90° C. All liquid was evaporated by heating the slurry at 90–100° C. The acid modified zeolite was dried at 90° C. and then calcined at a temperature between 500 and 530° C. under air for 10 hr. The calcined zeolite was then pressed and sized using 20 and 40 mesh screens for use in a reactor for toluene methylation reaction. BET surface area and total pore volume (measured by $N_2$ adsorption) for catalyst F are presented in Table 1 below.

TABLE 1

| Catalyst | Acid Treatment | | | | | | |
|---|---|---|---|---|---|---|---|
| | Zeolite, g | Water[a], ml | Acid[b], g | Water[c], ml | Wt % F | SA, $m^2/g$ | PV, ml/g |
| A | 4.02 | 47 | 1.24 | 0 | <0.037 | 329.0 | 0.243 |
| B | 8.00 | 191 | 2.43 | 191 | 0.047 | 298.3 | 0.230 |
| C | 5.06 | 10 | 2.01 | 0 | 0.088 | 312.7 | 0.233 |
| D | 5.02 | 10 | 4.00 | 0 | 0.206 | 279.6 | 0.232 |
| E | | | None | | | 375.0 | 0.244 |
| F | 25.33 | 50 | 10.41[d] | 0 | | 368.4 | 0.249 |

[a]Amount of water added to make zeolite slurry;
[b]Unless stated otherwise acid is 40% HF (in water);
[c]Amount of water added to 40% HF to further dilute prior to adding to zeolite slurry;
[d]$H_2SO_4$ (95–98%).

Examples 1–7

The catalysts A–E, as referenced in Table 1 and prepared as described above, were used in toluene methylation reactions. The reactions were each carried out in a fixed bed, continuous flow type reactor. In each case, the catalyst used was dried by slowly raising the catalyst bed temperature (about 5° C./min) to 200° C. under hydrogen ($H_2$) flow for at least one hour. A premixed toluene and methanol feed (molar ratio 2/1) was added to the reactor at 200° C. and the catalyst bed inlet temperature was increased to about 500° C. The liquid hourly space velocity (LHSV) based on toluene/methanol feed was maintained at about 31 $hr^{-1}$ and cofeed of $H_2$ gas was fed and maintained to provide a $H_2$/(toluene+methanol) molar ratio of about 0.1. Water was added to the hydrocarbon (HC, where HC=toluene+methanol) feed and was vaporized prior to introduction into the reactor. The $H_2O$/HC molar ratio was about 0.65 and the reactor pressure was about 20 psig. The following results were obtained, as presented in Table 2 below.

TABLE 2

| Catalysts for Toluene Methylation | | | | | | |
|---|---|---|---|---|---|---|
| | EXAMPLES | | | | | |
| | 1 | 2 | 3 | 4 | 5 | 6 |
| | Catalyst ID | | | | | |
| | A | B | C | D | E | F |
| Catalytic Performance Test | | | | | | |
| Catalyst Bed Inlet Temp/° C. | 500 | 503 | 503 | 506 | 500 | 504 |
| Reactor Inlet Pressure, psig | 21 | 23 | 21 | 22 | 23 | 22 |
| LHSV[a] | 31 | 31 | 31 | 31 | 30 | 30 |
| Cofeed H2O, mole/mole HC Feed | 0.65 | 0.65 | 0.65 | 0.65 | 0.66 | 0.66 |

TABLE 2-continued

Catalysts for Toluene Methylation

| | EXAMPLES | | | | | |
|---|---|---|---|---|---|---|
| | 1 | 2 | 3 | 4 | 5 | 6 |
| | | | Catalyst ID | | | |
| | A | B | C | D | E | F |
| Cofeed H2, mole/mole HC Feed | 0.11 | 0.11 | 0.11 | 0.11 | 0.11 | 0.11 |
| Product Distribution, wt %[b] | | | | | | |
| C5− | 1.34 | 2.21 | 1.48 | 3.34 | 1.71 | 3.34 |
| Dimethylether | 0.00 | 0.01 | 0.01 | 0.01 | 0.00 | 0 |
| Methanol | 0.00 | 0.44 | 0.37 | 0.01 | 0.53 | 0.48 |
| Benzene | 0.00 | 0 | 0.00 | 0 | 0.46 | 0.41 |
| Toluene | 62.21 | 65.37 | 66.42 | 65.00 | 61.44 | 64.16 |
| EthylBenzene | 0.00 | 0 | 0.00 | 0.07 | 0.00 | 0 |
| Para-Xylene (PX) | 18.12 | 21.66 | 20.26 | 20.61 | 10.00 | 9.33 |
| Meta-Xylene (MX) | 10.00 | 6.23 | 5.56 | 5.37 | 16.01 | 13.63 |
| Ortho-Xylene (OX) | 4.57 | 3.13 | 2.91 | 2.71 | 6.44 | 5.52 |
| EthylToluene | 0.27 | 0.31 | 0.33 | 0.33 | 0.78 | 1.03 |
| TrimethylBenzene | 3.07 | 0.26 | 2.34 | 2.18 | 2.40 | 1.92 |
| C10+ | 0.41 | 0.38 | 0.33 | 0.36 | 0.23 | 0.20 |
| Toluene Conv., mole % | 33.41 | 29.7 | 29.05 | 29.45 | 33.37 | 30.03 |
| Total Xylenes Selectivity, % | 89.72 | 97.02 | 90.56 | 90.67 | 89.33 | 88.81 |
| PX in Total Xylenes, % | 55.42 | 69.84 | 70.52 | 71.84 | 30.82 | 35.02 |

[a]Based on toluene and methanol feed.
[b]Excluding H$_2$O and normalized to 100%.

The fluoride-modified HZSM-5 zeolite showed an increase in p-xylene selectivity. For example, fluoride-modified HZSM-5 Catalysts A, B, C and D showed a 55%, 70%, 71% and 72% p-xylene content, respectively, in total xylenes compared to 31% p-xylene for non-modified ZSM-5 Catalyst E, when used in toluene methylation under the same reaction conditions. This represents at least a 50% increase in selectivity for para-isomers in aromatic alkylation reactions for the fluoride-treated catalyst compared to the same zeolite catalyst without such treatment under similar aromatic alkylation reaction conditions. As shown, increases in selectivity for para-isomers by as much as 80%, 100% or more compared to the same zeolite catalyst without such treatment used under similar aromatic alkylation reaction conditions can be obtained.

The sulfuric acid-modified Catalyst F did not show a significant increase in p-xylene selectivity, as compared to the non-modified Catalyst E.

Structurally, the fluoride-modified zeolite showed a reduction in BET surface area, while the total pore volume remained generally unchanged compared to the non-modified zeolite. The BET surface area of non-fluorided ZSM-5 catalyst (E) is 375 m$^2$/g, and that of fluorided ZSM-5 catalyst (D) 280 m$^2$/g.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of preparing an alkyl aromatic product comprising:
   modifying a ZSM-5-type zeolite catalyst by contacting a fresh, non-steamed ZSM-5-type zeolite catalyst with a fluoride-containing compound;
   providing the fluoride-modified ZSM-5-type zeolite catalyst within a reactor; and
   contacting the catalyst with an aromatic hydrocarbon and an alkylating agent under reaction conditions suitable for aromatic alkylation to form a di-alkyl aromatic product.

2. The method of claim 1, wherein the zeolite is contacted with a fluoride-containing compound through at least one of vapor phase fluoridation and liquid impregnation.

3. The method of claim 1, wherein the fluoride-containing compound is selected from a group consisting of F$_2$, HF, BF$_3$, NH$_4$F, NH$_4$BF$_4$, CF$_4$, CHF$_3$, CH$_2$F$_2$, CF$_3$COOH, CF$_3$OH, CF$_3$OCF$_3$, CF$_3$CH$_2$OH, SF$_6$, SO$_2$F$_2$, SOF$_2$ and NH$_4$SiF$_6$.

4. The method of claim 1, wherein the fluoride-treated zeolite catalyst exhibits at least a 50% selectivity for para-isomers.

5. The method of claim 1, wherein the ZSM-5-type zeolite catalyst has a silica to alumina molar ratio of from 200 to 1000.

6. The method of claim 1, wherein the fluoride-treated zeolite catalyst has a BET surface area that is at least 10% less than that of the same zeolite catalyst without such treatment.

7. The method of claim 1, wherein the fluoride-treated zeolite catalyst has a BET surface area of 350 m$^2$/g or less.

8. The method of claim 1, wherein the fluoride-treated zeolite catalyst contains at least 0.05 wt % F as measured by ASTM E-442.

9. The method of claim 1, wherein the ZSM-5-type zeolite catalyst has a silica to alumina ratio of from 200 or more.

10. A method of preparing an alkyl aromatic product comprising:
    providing a fluoride-treated ZSM-5-type zeolite catalyst having a silica to alumina molar ratio of from 200 or more and containing at least 0.05 wt % F as measured by ASTM E-442 within a reactor; and contacting the catalyst with an aromatic hydrocarbon and an alkylating agent under reaction conditions suitable for aromatic alkylation to form a di-alkyl aromatic product.

11. The method of claim 10, wherein the fluoride-treated ZSM-5 zeolite catalyst is treated with a fluoride-containing compound selected from a group consisting of $F_2$, HF, $BF_3$, $NH_4F$, $NH_4BF_4$, $CF_4$, $CHF_3$, $CH_2F_2$, $CF_3COOH$, $CF_3OH$, $CF_3OCF_3$, $CF_3CH_2OH$, $SF_6$, $SO_2F_2$, $SOF_2$ and $NH_4SiF_6$.

12. The method of claim 11, wherein the fluoride-containing compound is hydrofluoric acid (HF).

13. The method of claim 10, wherein the ZSM-5-type zeolite catalyst has a silica to alumina molar ratio of from 200 to 1000.

14. The method of claim 10, wherein the fluoride-treated zeolite has a BET surface area that is at least 10% less than that of the same zeolite catalyst without such treatment.

15. The method of claim 10, wherein the di-alkyl aromatic product contains at least 40% para-isomers of the di-alkyl aromatic product by total mixed-di-alkyl aromatic product when used in aromatic alkylation reactions.

16. The method of claim 10, wherein the zeolite is contacted with a fluoride-containing compound through vapor phase fluoridation.

17. A method of preparing a xylene product comprising:
providing a fluoride-treated ZSM-5-type zeolite catalyst within a reactor; and
contacting the catalyst with toluene/methanol feed under reaction conditions suitable for toluene methylation to form a xylene product containing at least 50% para-xylene by total mixed xylenes.

18. The method of claim 17, wherein the ZSM-5-type zeolite catalyst has a silica to alumina molar ratio of from 200 or more.

19. The method of claim 1, wherein:
the aromatic hydrocarbon is toluene, the alkylating is a methylating agent, and the di-alkyl aromatic hydrocarbon product is xylene, with a least 50% para-xylene selectivity of mixed xylenes being obtained.

* * * * *